US009375303B1

(12) United States Patent
Cook et al.

(10) Patent No.: US 9,375,303 B1
(45) Date of Patent: Jun. 28, 2016

(54) METHODS OF ORDERING AND MANUFACTURING ORTHOPEDIC COMPONENTS

(75) Inventors: Kevin S. Cook, Warsaw, IN (US); James E. Grimm, Winona Lake, IN (US); Anthony P. Romano, Columbia City, IN (US)

(73) Assignee: Zimmer, Inc., Warsaw, IN (US)

( * ) Notice: Subject to any disclaimer, the term of this patent is extended or adjusted under 35 U.S.C. 154(b) by 234 days.

(21) Appl. No.: 13/087,081

(22) Filed: Apr. 14, 2011

Related U.S. Application Data

(60) Provisional application No. 61/324,525, filed on Apr. 15, 2010.

(51) Int. Cl.
*A61F 2/30* (2006.01)
*A61F 2/00* (2006.01)

(52) U.S. Cl.
CPC ........... *A61F 2/0095* (2013.01); *A61F 2/30942* (2013.01)

(58) Field of Classification Search
CPC ..................... A61B 2019/02; A61B 2019/026; A61B 2019/2071; G06F 2219/10
See application file for complete search history.

(56) References Cited

U.S. PATENT DOCUMENTS

| | | |
|---|---|---|
| 4,501,269 A | 2/1985 | Bagby |
| 4,704,686 A | 11/1987 | Aldinger |
| 4,710,193 A | 12/1987 | Volk |
| 4,936,862 A | 6/1990 | Walker et al. |
| 5,067,964 A | 11/1991 | Richmond et al. |
| 5,112,354 A | 5/1992 | Sires |
| 5,147,404 A | 9/1992 | Downey |
| 5,370,692 A | 12/1994 | Fink |
| 5,374,813 A * | 12/1994 | Shipp ........................... 235/375 |
| 5,382,164 A | 1/1995 | Stern |
| 5,527,182 A | 6/1996 | Willoughby |
| 5,587,912 A | 12/1996 | Andersson et al. |
| 5,676,255 A * | 10/1997 | Flowers ........................... 209/2 |
| 5,798,062 A | 8/1998 | Thielbar |
| 5,824,081 A | 10/1998 | Knapp et al. |
| 5,876,443 A | 3/1999 | Hochmair et al. |
| 5,880,826 A | 3/1999 | Jung et al. |

(Continued)

FOREIGN PATENT DOCUMENTS

| | | |
|---|---|---|
| WO | WO2009/025783 A1 | 2/2009 |
| WO | WO2010/099359 A1 | 9/2010 |
| WO | WO2010/099360 A1 | 9/2010 |

*Primary Examiner* — Ryan Jarrett
(74) *Attorney, Agent, or Firm* — Schwegman Lundberg & Woessner, P.A.

(57) ABSTRACT

Methods of ordering and manufacturing orthopedic components eliminate the need to stockpile and inventory large volumes of implants and instruments. In one exemplary embodiment, the surgeon begins by acquiring anatomical data from a patient. The anatomical data may then be loaded into a data comparison program. The data comparison program performs a best-fit analysis by comparing the patient's anatomical data to a number of predesigned, tested, and validated virtual implant models that are stored in a database. Once an implant has been identified by the data comparison program for the individual patient, the surgeon may place an order electronically with the manufacturer via the internet. In one exemplary embodiment, when placing the order, the surgeon will specify the type of implant, the surgery date, specific patient information, shipping information, and the preferred surgical technique that the surgeon anticipates using.

19 Claims, 4 Drawing Sheets

(56) References Cited

U.S. PATENT DOCUMENTS

| | | | |
|---|---|---|---|
| 5,938,633 A * | 8/1999 | Beaupre | 604/22 |
| 6,328,567 B1 | 12/2001 | Morris et al. | |
| 6,450,807 B1 | 9/2002 | Chishti et al. | |
| 6,459,948 B1 | 10/2002 | Ateshian et al. | |
| 6,463,351 B1 | 10/2002 | Clynch | |
| 6,468,314 B2 | 10/2002 | Schwartz et al. | |
| 6,640,150 B1 | 10/2003 | Persson et al. | |
| 6,772,026 B2 * | 8/2004 | Bradbury et al. | 700/98 |
| 6,846,179 B2 | 1/2005 | Chapouland et al. | |
| 6,988,015 B1 | 1/2006 | Schopf et al. | |
| 7,045,141 B2 | 5/2006 | Merboth et al. | |
| 7,089,070 B1 | 8/2006 | Andersson et al. | |
| 7,153,135 B1 | 12/2006 | Thomas | |
| 7,320,404 B2 | 1/2008 | Landis | |
| 7,338,524 B2 | 3/2008 | Fell et al. | |
| 7,363,239 B1 | 4/2008 | Andersson et al. | |
| 7,635,371 B2 | 12/2009 | McGahan et al. | |
| 7,983,777 B2 * | 7/2011 | Melton et al. | 700/98 |
| 8,186,587 B2 * | 5/2012 | Zmood et al. | 235/385 |
| 2002/0019660 A1 | 2/2002 | Gianotti et al. | |
| 2002/0042038 A1 | 4/2002 | Miller et al. | |
| 2002/0082623 A1 | 6/2002 | Osther et al. | |
| 2004/0023183 A1 | 2/2004 | Miller et al. | |
| 2005/0095552 A1 | 5/2005 | Sporbert et al. | |
| 2005/0131396 A1 * | 6/2005 | Stanczak et al. | 606/1 |
| 2007/0010875 A1 | 1/2007 | Trout et al. | |
| 2007/0083286 A1 * | 4/2007 | Kobayashi | 700/214 |
| 2007/0118055 A1 * | 5/2007 | McCombs | 600/587 |
| 2007/0118243 A1 * | 5/2007 | Schroeder et al. | 700/118 |
| 2007/0255288 A1 | 11/2007 | Mahfouz et al. | |
| 2008/0272023 A1 * | 11/2008 | McCormick | A61B 19/026 206/570 |
| 2009/0043556 A1 * | 2/2009 | Axelson et al. | 703/11 |
| 2009/0048597 A1 | 2/2009 | Heavener et al. | |
| 2009/0144091 A1 * | 6/2009 | Rago | 705/3 |
| 2009/0248044 A1 | 10/2009 | Amiot et al. | |
| 2010/0140124 A1 | 6/2010 | Hafner | |
| 2010/0152782 A1 | 6/2010 | Stone et al. | |
| 2010/0217246 A1 * | 8/2010 | Reeves et al. | 606/1 |
| 2010/0217270 A1 * | 8/2010 | Polinski et al. | 606/87 |
| 2011/0160743 A1 * | 6/2011 | Espinal | 606/129 |
| 2011/0305379 A1 * | 12/2011 | Mahfouz | 382/131 |

* cited by examiner

METHODS OF ORDERING AND MANUFACTURING ORTHOPEDIC COMPONENTS

CROSS-REFERENCE TO RELATED APPLICATIONS

This application claims the benefit under 35 U.S.C. §119(e) of U.S. Provisional Patent Application Ser. No. 61/324,525, filed Apr. 15, 2010 and entitled METHODS OF ORDERING AND MANUFACTURING ORTHOPEDIC COMPONENTS, the entire disclosure of which is hereby expressly incorporated herein by reference.

BACKGROUND

1. Technical Field

The present disclosure relates to methods of ordering and manufacturing orthopedic components.

2. Description of the Related Art

Orthopedic components are generally manufactured in various sizes and in mass quantities which are then provided to distributors. The distributors fulfill individual sales orders that may be received from a customer, such as a hospital, surgeon, or sales person. While this distribution process is effective, it results in large inventory costs for both the manufacturer and the distributor.

For example, in some cases a particular prosthesis design may be offered in six or seven different sizes to accommodate natural variations inherent in anatomical structures. Each of these implant sizes may in turn be offered in two or three style variations. In addition to the resulting large quantity of available prostheses conforming to one particular design, multiple additional implant designs may also be offered in a similar array of sizes and styles.

Thus, in order for the manufacturer and/or distributor to fulfill orders for any implant design, size and style, large quantities of various orthopedic implants must be maintained in inventory. The manufacturer must maintain large quantities of various implant sizes and related surgical instruments to provide to distributors, and distributors must also stock significant quantities of implants and instruments to readily fulfill orders from the end user.

Additionally, as a result of having a large volume of inventory, when an implant or instrument becomes obsolete, this inventory must be disposed of and results in a total economic loss to the manufacturer and the distributor. Additionally, due to the large volume of inventories that must be manufactured and inventoried in order to fulfill customer orders, product launches may be delayed while an inventory of the product, such as an implant or instrument, is stockpiled.

While known manufacturing and distribution methods are effective, what is needed is an improvement over the foregoing.

SUMMARY

The present disclosure provides methods of ordering and manufacturing orthopedic components that eliminate the need to stockpile and inventory large volumes of implants and instruments. In one exemplary embodiment, the surgeon begins by acquiring anatomical data from a patient. The anatomical data may then be loaded into a data comparison program. The data comparison program performs a best-fit analysis by comparing the patient's anatomical data to a number of predesigned, tested, and validated virtual implant models that are stored in a database. Once an implant has been identified by the data comparison program for the individual patient, the surgeon may place an order electronically with the manufacturer via the internet. In one exemplary embodiment, when placing the order, the surgeon will specify the type of implant, the surgery date, specific patient information, shipping information, and the preferred surgical technique that the surgeon anticipates using.

Once the order is placed by surgeon, the order is received by the implant manufacturer and a manufacturing work order is generated. The manufacturer then generates the components that have been ordered using known manufacturing techniques. In one exemplary embodiment, the order may include both the implant and the corresponding instruments that are used during surgery to facilitate implantation of the implant. In one exemplary embodiment, the instruments that are to be used during the surgery are manufactured from a recyclable material, such as ultra high molecular weight polyethylene ("UHMWPE"). Once manufactured, the implant and instruments may then be packaged in a single kit that is sterilized and shipped directly to the requesting customer.

Once the implant and instrument kit is received by the customer, the kit is transported to the operating room where the patient has been prepped and the joint opened using standard techniques. Then, by using the instruments contained within the single kit, the surgeon performs the required surgery and implants the implant. Once the surgery is completed, the used instruments may be returned to the container and the lid of the container resealed thereon. The sealed container and its contents may then be returned to a central receiving location, such as the manufacturer. The entire container may then be destroyed and/or recycled, eliminating the need to sterilize and otherwise track the instruments within the hospital or operating room.

Advantageously, the present disclosure allows for an individual patient to be provided with the best fitting prosthesis that is currently available for their individual anatomy. Additionally, by utilizing just-in-time manufacturing, i.e., manufacturing a component only when their order for the component is received, the cost of inventorying components for both the manufacturer and the distributor are eliminated. Further, by packaging all of the components in a single container as a single kit, a surgeon is ensured that all of the components necessary to complete the procedure are present in the operating room at the time the operation is performed. Additionally, since the instruments may be returned in the same container to the central receiving location, no cleaning or sterilization of the instruments by the hospital is required, operating room cleanup time is reduced, and the need to track the location of the instruments is eliminated.

In one form thereof, the present disclosure provides a method of ordering and manufacturing an implant and related instruments, comprising the steps of: receiving anatomical data collected from a patient; comparing the anatomical data to a database of implant designs; identifying an implant design from the implant designs in the database based on a result of the step of comparing the anatomical data to a database of implant designs; manufacturing an implant based on the identified implant design; manufacturing at least one instrument for use in implanting the implant; packaging the implant and the instrument in at least one container; contemporaneously shipping the implant and the instrument in the at least one container to a customer; and receiving the at least one container after the at least one instrument has been used.

In another form thereof, the present disclosure provides a surgical implant management system, comprising: data collection means for collecting anatomical data from a patient; an implant database including a plurality of implant designs;

data comparison means for comparing the anatomical data to the plurality of implant designs; identifying means for cooperating with the data comparison means to identify at least one matching implant, the matching implant closely matching the anatomical data; ordering means for communicating identifying information about the matching implant to an implant manufacturer; at least one implant instrument for use in implanting the matching implant; packaging means for contemporaneous delivery of the matching implant and the implant instrument from the implant manufacturer to a customer; and instrument return means for returning the implant instrument to the implant manufacturer after use.

BRIEF DESCRIPTION OF THE DRAWINGS

The above-mentioned and other features and advantages of this disclosure, and the manner of attaining them, will become more apparent and the disclosure itself will be better understood by reference to the following description of an embodiment of the disclosure taken in conjunction with the accompanying drawings, wherein.

Corresponding reference characters indicate corresponding parts throughout the several views. The exemplifications set out herein illustrate exemplary embodiments of the invention, and such exemplifications are not to be construed as limiting the scope of the disclosure in any manner.

DETAILED DESCRIPTION

For the purposes of promoting an understanding of the principles of the disclosure, reference will now be made to the embodiments illustrated in the drawings, which are described below. The embodiments disclosed below are not intended to be exhaustive or limit the disclosure to the precise form disclosed in the following detailed description. Rather, the embodiments are chosen and described so that others skilled in the art may utilize their teachings. It will be understood that no limitation of the scope of the disclosure is thereby intended. The disclosure includes any alterations and further modifications in the illustrated devices and described methods and further applications of the principles of the disclosure which would normally occur to one skilled in the art to which the disclosure relates.

The detailed descriptions which follow are presented in part in terms of algorithms and symbolic representations of operations on data bits within a computer memory representing alphanumeric characters or other information. These descriptions and representations are the means used by those skilled in data processing arts to most effectively convey the substance of their work to others skilled in the art.

An algorithm is here, and generally, conceived to be a self-consistent sequence of steps leading to a desired result. These steps are those requiring physical manipulations of physical quantities. Usually, though not necessarily, these quantities take the form of electrical or magnetic signals capable of being stored, transferred, combined, compared, and otherwise manipulated. It proves convenient at times, principally for reasons of common usage, to refer to these signals as bits, values, symbols, characters, display data, terms, numbers, or the like. It should be borne in mind, however, that all of these and similar terms are to be associated with the appropriate physical quantities and are merely used here as convenient labels applied to these quantities.

Some algorithms may use data structures for both inputting information and producing the desired result. Data structures greatly facilitate data management by data processing systems, and are not accessible except through sophisticated software systems. Data structures are not the information content of a memory; rather they represent specific electronic structural elements which impart a physical organization on the information stored in memory. More than mere abstraction, the data structures are specific electrical or magnetic structural elements in memory which simultaneously represent complex data accurately and provide increased efficiency in computer operation.

Further, the manipulations performed are often referred to in terms, such as comparing or adding, commonly associated with mental operations performed by a human operator. No such capability of a human operator is necessary, or desirable in most cases, in some of the operations described herein which form part of the present disclosure; rather, the operations are machine operations. Useful machines for performing these operations of the present disclosure include general purpose digital computers or other similar devices. In all cases the distinction between the method operations in operating a computer and the method of computation itself should be recognized. The present disclosure relates to a method and apparatus for operating a computer in processing electrical or other (e.g., mechanical, chemical) physical signals to generate other desired physical signals.

The present disclosure also relates to an apparatus for performing these operations. This apparatus may be specifically constructed for the required purposes or it may comprise a general purpose computer as selectively activated or reconfigured by a computer program stored in the computer. The algorithms presented herein are not inherently related to any particular computer or other apparatus. In particular, various general purpose machines may be used with programs written in accordance with the teachings herein, or it may prove more convenient to construct more specialized apparatus to perform the required method steps. The required structure for a variety of these machines will be apparent from the description below.

A general purpose computer suitable for use with the present disclosure, in addition to containing the specialized instructions for performing the operations described in detail below, may also include operating system software. An exemplary operating system software is a WINDOWS operating system available from Microsoft Corporation of Redmond, Wash. Users of the computer activate computer programs or network resources to create "processes" which include both the general operation of the computer program along with specific operations.

The present disclosure deals with "object-oriented" software, and particularly with an "object-oriented" operating system. The "object-oriented" software is organized into "objects," each comprising a block of computer instructions describing various procedures ("methods") to be performed in response to "messages" sent to the object or "events" which occur with the object. Such operations include, for example, the manipulation of variables, the activation of an object by an external event, and the transmission of one or more messages to other objects.

Both programs and databases may be objects. In the case of databases, the data portion of the object may be significantly larger than the methods portion. The actual physical implementation of a database on a general purpose computer may take several forms, from complete individual records storing the substantive information with several key indexes for locating a particular record, to a plurality of tables interrelated by relational operations, to a matrix of cross-linked data records, to various combinations and hybrids of these general types. In particular physical devices, a database may be structured and arranged to accommodate the restrictions of the physical device—but when transferred to a general purpose computer be able to be stored in a variety of formats. Thus, while certain types of information may be described as being stored in a "database" from a conceptual standpoint, generally such information may be electronically stored in a variety of structures with a variety of encoding techniques.

Databases may contain many types of information, and may store the information in a variety of encoding techniques. When a database stores information that relates to a particular person, product, location, or other thing, the database typically uses a unique identifier that binds the "concept" of the person, product, location, or other thing with a storable piece or set of data. When the unique identifier is used to reference the data record, the unique identifier is termed a "key" and data records associated with the "concept" are said to be "keyed" by the unique identifier. The association between a key and its data may be implemented in a variety of ways, for example by having the key be a field in a corresponding data record, by having a key value in a search tree with an associated pointer to one or more data records corresponding to the key, or by encoding the corresponding information with a value that, upon decoding, produces the unique identifier and the corresponding data, etc. By these various methods, instances of data may be associated with, or "bound" with or to, the "concept" by using the key. In the context of the present disclosure (and as described in greater detail below), a virtual model of a particular patient's anatomy (i.e., an articular surface of a bone) may be keyed to a data record for a particular "best fit" implant component.

A general purpose computer for use with the present disclosure may include communications software which allows the computer to communicate with one or more computer networks, such as a local area network, a wide area network, a public switched network, any type of wired network, any type of wireless network, and combinations thereof. An exemplary public switched network is the Internet. Exemplary communications software includes browser software, and other types of software which permit the computer to communicate with other devices across a network. In one embodiment, the computer also communicates with one or more additional general purpose computers over a network, such as remote computers forming part of a hospital network or surgery center network (as described in detail below).

The terms "network," "local area network," "LAN," "wide area network," or "WAN" mean two or more computers which are connected in such a manner that messages may be transmitted between the computers. In such computer networks, typically one or more computers operate as a "server," a computer with large storage devices such as hard disk drives and communication hardware to operate peripheral devices such as printers or modems. Other computers, termed "workstations," provide a user interface so that users of computer networks can access the network resources, such as shared data files, common peripheral devices, and inter-workstation communication.

The computers have at least one processor for executing machine instructions, and memory for storing instructions and other information. Many combinations of processing circuitry and information storing equipment are known by those of ordinary skill in these arts. A processor may be a microprocessor, a digital signal processor ("DSP"), a central processing unit ("CPU"), or other circuit or equivalent capable of interpreting instructions or performing logical actions on information. Memory includes both volatile and non-volatile memory, including temporary and cache, in electronic, magnetic, optical, printed, or other format used to store information. Memory may be located either locally with the computer (removably or non-removably), or may be accessible across the network. By way of example, a computer-readable medium suitable as memory may include, but is not limited to, RAM, ROM, EEPROM, flash memory or other memory technology, CD-ROM, Digital Versatile Disk (DVD) or other optical disk storage, magnetic cassettes, magnetic tape, magnetic disk storage or other magnetic storage devices, or any other medium which may be used to store the desired information and which may be accessed by the computer.

While a general purpose computer may be provided for performing the computational and memory storage tasks described herein, it is also contemplated that such tasks may be spread out across various computing and memory-storage resources connected via a network. Such a network based distribution of computing and memory storage resources may be referred to as "cloud" computing. For example, the memory which stores the data comparison program may be located in a remote memory storage unit, where the data comparison program may be pooled with other stored programs (which may or may not be related to the data comparison program). Similarly, the computer processor responsible for executing machine instructions (i.e., for executing the data comparison program) may be located in location remote from the memory storage unit and connected thereto via the network.

The present disclosure provides a method for ordering and manufacturing orthopedic implants and/or instruments. As described below, a system in accordance with the present disclosure may include a data comparison program. The data comparison program is run by a computer and operates to compare an individual patient's anatomical data against a plurality of individual implant models, e.g., an implant database, to identify a particular implant that best matches an individual patient's anatomy. In one exemplary embodiment, the data comparison program includes a database having information related to different implant types and specific sizes and designs of implants within each implant type. For example, knee implants may be identified within the database as having both femoral components and tibial components. Additional information about each individual component is also contained within the database. For example, for a femoral component adapted to replace the articular surfaces at the distal end of a femur, the width of the medial and lateral condyles, the height and width of the patello-femoral flange, and the overall implant height and width of the femoral component may be entered into and stored in the database. Then, if a surgeon requests a femoral component for an individual patient, the surgeon will enter the available, patient specific information. Then, the data comparison program will compare the patient specific information to each of the femoral components within the database to determine which of the femoral components provides the best overall fit for the individual patient, as described in detail below.

In one exemplary embodiment, the database may be stored in a first location, such as in the memory of a server managed by an implant manufacturer. The patient information may be transmitted or otherwise provided to the data comparison program via the internet if the data input location is remote, such as where the patient information is entered at a hospital or doctor's office. Alternatively, the patient information may be transmitted by a direct network connection, such as from a terminal connected directly to the implant manufacturer's server. In another exemplary embodiment, the implant database may be stored in the surgeon's individual computer, which in turn runs the data comparison program using patient-specific data entered by the surgeon.

Once the data comparison program has identified the most appropriate implant based on a patient's individual anatomy, an order may be placed to request that the implant manufacturer initiate the manufacture of the implant. In one exemplary embodiment, the order is placed by the surgeon via the internet. In another exemplary embodiment, the order is placed over a network. Once the order is received, the manufacturer may create the implant and package the implant with related unused instruments for shipment to the consumer, such as in the manner described in detail below. After the implantation of the implant, the used instruments may be returned to the manufacturer for disposal.

Figure 1A:
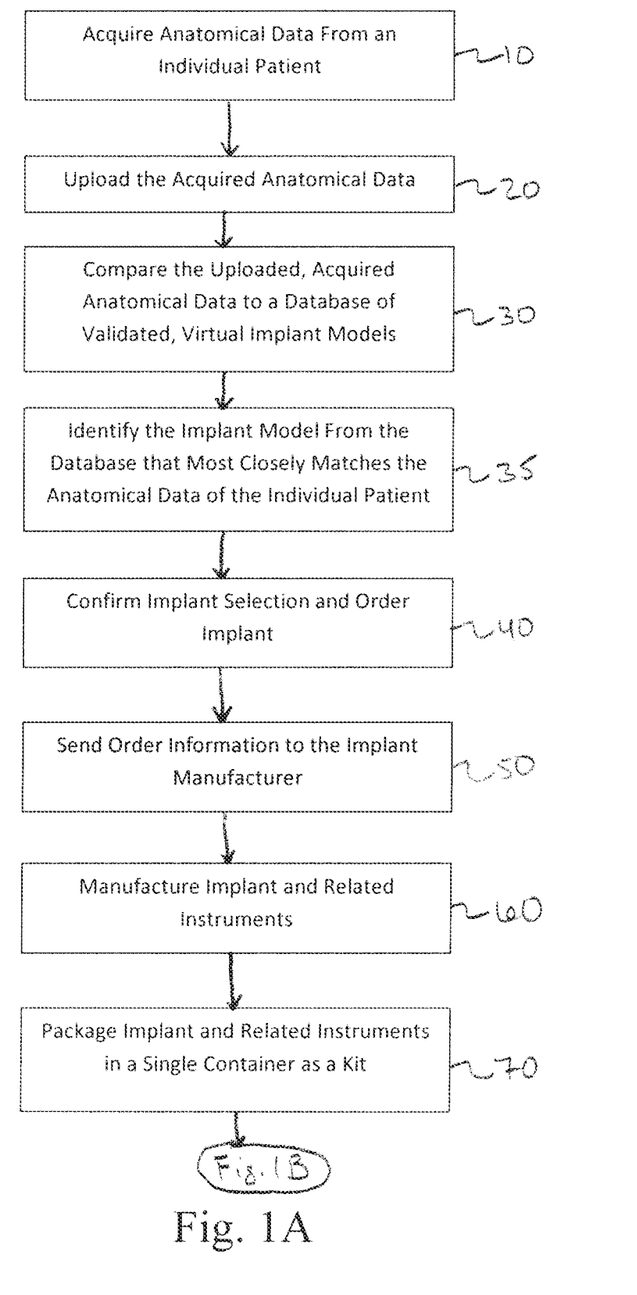
FIGS. 1A and 1B provide a flow chart of the steps of an exemplary embodiment of the present disclosure.
Figure 1B:
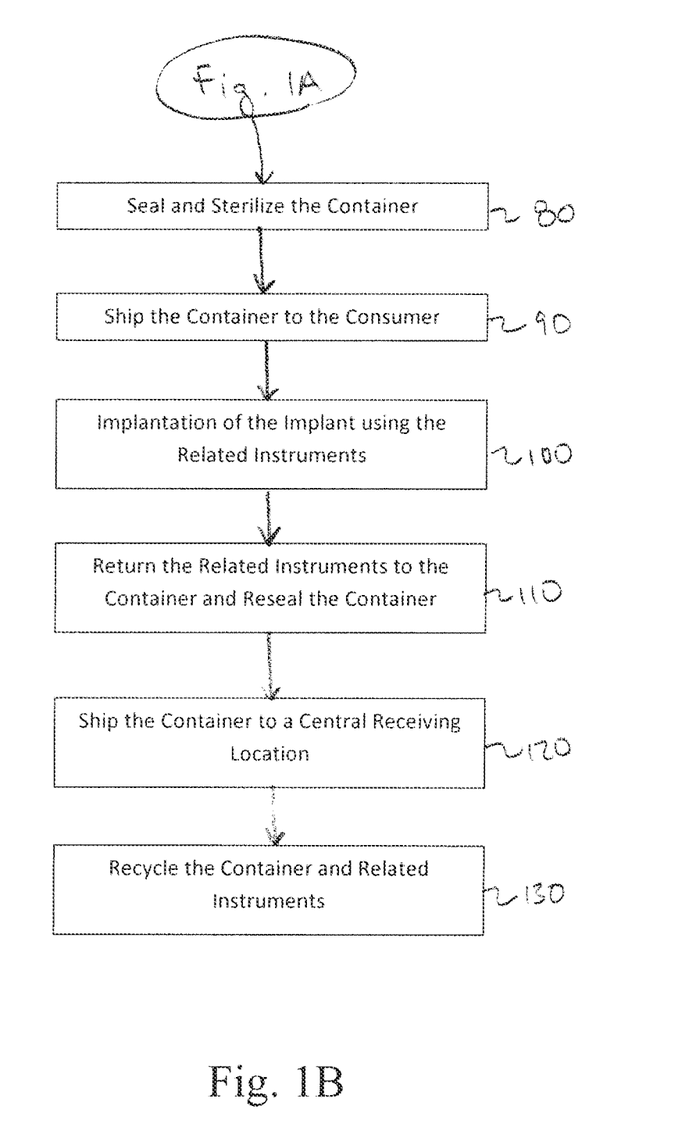

Turning now to FIGS. 1A and 1B, a flow chart illustrating the steps of an exemplary embodiment of the present disclosure is shown. Specifically, referring to Step 10, a surgeon begins by acquiring anatomical data from an individual patient that may be provided to the data comparison program. In one exemplary embodiment, the anatomical data is collected by collecting a series of two-dimensional X-ray images, then combining the images to form a three-dimensional model of the patient's anatomy.

In another exemplary embodiment, accelerometers are used to track the motion of respective articular surfaces in the patient's joint as the joint is articulated through its range of motion. The tracked motion is collected to create a data set. The data set is manipulated using a software program to provide an overview or map of an individual patient's knee joint motion. An exemplary method and apparatus for characterizing a joint by tracking articulation is described in U.S. patent application Ser. No. 12/854,610, filed Aug. 11, 2010 and entitled VIRTUAL IMPLANT PLACEMENT IN THE OR, which commonly assigned with the present application, the entire disclosure of which is hereby expressly incorporated by reference herein.

In other exemplary embodiments, magnetic resonance imaging (MRI), computed tomography (CT), positron emission tomography (PET), X-ray, ultrasound, or any other imaging modality may be used to identify and characterize the patient's individual anatomy. Once the patient's individual anatomy has been determined, a data file containing the patient's individual anatomical information may be created and stored. The data file containing such anatomical information may be generated using any of the methods disclosed in the following documents, all of which are commonly assigned with the present application, the entire disclosures of which are hereby expressly incorporated by reference herein: Patent Cooperation Treaty Application Publication No. WO 2010/099360, filed Feb. 25, 2010 and entitled CUSTOMIZED ORTHOPAEDIC IMPLANTS AND RELATED METHODS; Patent Cooperation Treaty Application Publication No. WO 2009/025783, filed Aug. 18, 2008 and entitled IMPLANT DESIGN ANALYSIS SUITE; Patent Cooperation Treaty Application Publication No. WO 2010/099359, filed Feb. 25, 2010 and entitled CUSTOMIZED ORTHOPAEDIC IMPLANTS AND RELATED METHODS; U.S. patent application Ser. No. 11/685,906, filed Mar. 14, 2007 and entitled METHODS OF PREDETERMINING THE CONTOUR OF A RESECTED BONE SURFACE AND ASSESSING THE FIT OF A PROSTHESIS ON THE BONE; U.S. patent application Ser. No. 12/410,884, filed Mar. 25, 2009 and entitled METHOD AND SYSTEM FOR PLANNING/GUIDING ALTERATIONS TO A BONE; U.S. patent application Ser. No. 12/410,854, filed Mar. 25, 2009 and entitled TRACKING SYSTEM AND METHOD; and U.S. Provisional Patent Application Ser. No. 61/342,873, filed Apr. 21, 2010 and entitled SYSTEM AND METHOD FOR ASSESSING IMPLANT FIT TO AN ANATOMICAL FEATURE.

Referring now to Step 20, once a patient's anatomical data has been acquired and/or a data file created, the data may be uploaded to the computer running the data comparison program. In one exemplary embodiment, data files containing each of the two-dimensional X-ray images are uploaded to the computer running the data comparison program. In this embodiment, the data comparison program may also include a data manipulation program that accesses the uploaded data files and combines the two-dimensional X-rays into a three-dimensional model. The data comparison program can then extract specific measurements of the individual patient's anatomy for later comparison to implant information contained in the database.

Similarly, in one exemplary embodiment, the data comparison program may include an additional module that allows for uploaded accelerometer data to be mapped to show joint motion. Once the patient's individual anatomical data is collected according to the methods described herein, the anatomical data is uploaded to the computer running the data comparison program. Other data provided to the data comparison program may include, for example, the type of implant desired, the surgery date and any relevant patient information, shipping information, and a preferred surgical technique that the surgeon may anticipate using for the implantation of the implant.

The data comparison program accesses the uploaded data and performs a comparison of the patient's anatomical data to a database containing information related to validated virtual implant models, as described in detail above, at Step 30. In an exemplary embodiment, the validated implant designs of the implant database are designs that have undergone standardized analyses, such as risk assessment analysis, design verification, design testing and validation, regulatory submissions, and other analyses. These standardized analyses, or design controls, have the potential to constrain or alter features and geometrical configurations incorporated into a design. In contrast, the features and geometrical configurations of a custom implant design are generally specified by an individual surgeon, and are not subject to the design controls of a validated implant design. For example, a validated implant may be subject to regulatory approval (such as from the Food and Drug Administration of the United States), while a custom implant may be considered a "prescription" device and thus may not be subject to the same regulatory approval requirements.

By comparing specific information about the individual patient's anatomy to information about specific implant designs stored in the database, the data comparison program identifies the implant that best matches the individual's anatomical data at Step 35. This "best-fit" implant is displayed on a monitor for review by the surgeon, who is provided with an opportunity to review the system's chosen implant. An exemplary method and apparatus for comparing the anatomical data to various implant characteristics and determining a "best-fit" implant is described in U.S. patent application Ser. No. 11/685,906 entitled METHODS OF PREDETERMINING THE CONTOUR OF A RESECTED BONE SURFACE AND ASSESSING THE FIT OF A PROSTHESIS ON THE BONE, which is incorporated by reference above.

Alternatively, the surgeon (or another person) may perform the comparison of step 30 manually by templating. Templating is accomplished by a person performing a comparison of various aspects of the collected anatomical data to templates representative of one or more implants. For example, a certain two-dimensional X-ray image may be overlaid on a corresponding two-dimensional schematic representation (i.e., a template) of an implant or implants. The shape of implant shown on the template is visually compared and contrasted to the anatomic X-ray. This process is iteratively repeated with various templates until a satisfactory comparison between the implant template and the anatomic structures is achieved. Exemplary methods and apparatuses for templating are described in U.S. patent application Ser. No. 11/458,257, filed Jul. 18, 2006 and entitled METHOD FOR SELECTING MODULAR IMPLANT COMPONENTS, and in U.S. patent application Ser. No. 11/616,369, filed Dec. 27, 2006 and entitled METHOD FOR SELECTING MODULAR IMPLANT COMPONENTS, both of which are commonly assigned with the present application, the entire disclosures of which are hereby expressly incorporated herein by reference.

The surgeon may make changes as desired, including selecting a different implant or modifying the data previously entered and/or calculated by the data comparison program. This may be required, for example, in a situation where the collected anatomical data includes deformity or tissue damage, and the data comparison algorithm may not sufficiently detect, characterize, and/or account for such anomaly. For example, where a deformity is diagnosed (such as by pre-operative imaging, as discussed above), the surgeon may make an intra-operative decision to correct for such deformity using augmentation or other suitable surgical tools and methods. To the extent necessary, the system of the present disclosure allows the surgeon to manually select an appropriate implant to ensure compatibility with his or her chosen method of deformity correction.

In one exemplary embodiment, the data comparison program may display multiple implants for review by the surgeon. For example, the surgeon may reject the "best-fit" implant identified at step 35. The surgeon may then be presented with a "second-best-fit" implant identified by the data comparison program. To identify the second-best-fit implant, the data comparison program again identifies the implant that best matches the individual's anatomical data from the database of implants in the same manner as described above with respect to steps 30 and 35, except that the previously-identified best-fit implant is excluded from the database. The surgeon may then review and accept or reject the second-best-fit implant. If the surgeon rejects the second-best-fit implant, steps 30 and 35 are again performed with the best-fit and second-best-fit implants excluded from the database, resulting in identification of a third-best-fit implant. This process may continue iteratively until the surgeon identifies an acceptable implant.

Once the surgeon selects a satisfactory implant, the surgeon may, at Step 40, confirm the selection and cause an order for the implant to be automatically placed with the manufacturer over the internet or another computer network.

At Step 50, after the order is confirmed by the surgeon, the communications software may direct the order information to a customer service department of an implant manufacturer, and/or may generate a manufacturing work order that is provided directly to the manufacturing department of the manufacturer.

Steps 20 through 50 may be accomplished using any of the methods and apparatuses disclosed in the foregoing and in the following patent applications, all of which are incorporated by reference above: Patent Cooperation Treaty Application Publication Nos. WO 2010/099360, WO 2009/025783, and WO 2010/099359; U.S. patent application Ser. Nos. 11/685,906, 12/410,884, and 12/410,854; and U.S. Provisional Patent Application Ser. No. 61/342,873.

By identifying the implant that most closely approximates the patient's individual anatomy from the implant database, the patient and surgeon are assured that the implant will have the best possible fit of any implant within the database. Additionally, the implant selected by the data comparison program is not limited by inventory constraints, because the implant can be manufactured specially for the placed order or sourced directly from existing inventory, if available. Thus, a system made in accordance with the present disclosure eliminates the need to inventory and manufacture a large number of individual implants.

Further, by providing, in one embodiment, internet based access to the data comparison program, the ability to identify the best implant for an individual patient is not geographically limited. In some instances, for example, specific implants are made available for particular population subsets within a geographical area. An example may include specialized implants adapted for compatibility with the anatomical features of Asian patients, in which these specialized implants are made available primarily in Asian countries. However, implants adapted for particular population subsets may not be readily available to surgeons in markets where the patient population lacks a significant presence.

Using a network-based ordering system in accordance with the present disclosure, a full range of population-specific implants may be included in the implant database. Thus, for example, a surgeon treating an Asian patient in the United States can use the data comparison program, discussed above with respect to steps 30 and 35, to compare the patient's unique anatomical features to a wider range of implants than would normally be available. Because the implant can be custom-manufactured to satisfy the surgeon's specific order, the inventory available in the surgeon's geographical area will not limit the surgeon's implant choices. Alternatively, the specific chosen implant may be sourced from existing inventories, including overseas inventories, and shipped to the surgeon.

Referring to Step 60, once an order has been received by the manufacturer, the requested implant and related instruments are manufactured. In one exemplary embodiment, when a work order is generated, implant models, computer and numerical programs, inspection programs, and package setup information may also be generated by an additional module of the data comparison program. This information may then be used by the manufacturing department to quickly and efficiently generate the individual implant. Alternatively, the individual implant may be generated using known manufacturing techniques without the generation of individual manufacturing plans by the data comparison program.

In an exemplary embodiment, the manufacturer may carry a stock of "maximum material" implants which have the greatest material thicknesses of any of a range of implants for a given implant size. The surgeon begins by choosing the size of the implant based on a planned series of cuts in the distal femur (sometimes referred to as "box cuts"), which in turn are a function of the size and shape of an individual patient's anatomy. A plurality of implants are then displayed which match the chosen implant size, such that each displayed implant has a configuration of bone-contacting surfaces that will fit the proposed series of cuts in the distal femur. After the surgeon chooses one of the displayed implants and places an order for the same, the manufacturer can remove material from a "maximum material" implant, apply any finishing processes as required or desired, and ship the prepared implant to the surgeon. Because this manufacturing process only involves material removal (such as by milling, grinding or other machining processes) and finishing steps, the newly prepared implant can be quickly produced and delivered.

In one embodiment, a central clearing house may be utilized to manage a pre-existing inventory of pre-manufactured implants. Such a central clearing house may include, for example, commonly used implant sizes and styles so that orders for such implants can be quickly satisfied from existing stock. Replacements for implants taken from the existing inventory may be manufactured as inventories are depleted.

In an exemplary embodiment, the individual implant may be manufactured immediately after receipt of the order and be ready for shipment, thereby effectuating "just-in-time" delivery of the implant. Such delivery not only reduces inventory and implant management complications, but ultimately provides the patient with a patient-specific implant which has been tailored to provide the best fit possible. As noted above, a wide range of standard, validated implant designs are included in the implant database. However, it is contemplated that a custom implant design may be created and manufactured to satisfy an order in some instances.

In one exemplary embodiment, instruments may be manufactured for use with the individual implant from a recyclable or disposable material, such as UHMWPE. Advantageously, by forming the instruments from a polymer or other recyclable or disposable material, the instruments need not be sterilized for subsequent reuse or otherwise retained by the hospital, as discussed in detail below.

Once the manufacture of the implant and instruments is complete, the implant and the new, unused instruments are packaged together into a single kit or container 200 (FIG. 2) at Step 70 (FIG. 1A). Container 200 prepared at Step 70 may contain the selected individual implant 210, packaged together with all of the instruments associated with an individual patient's surgery. Instruments included in the kit may include, for example, those instruments necessary to prepare the bone for implantation of the implant. The instruments 220 may include alignment guides, cut guides, drill guides, pin guides, patient-specific guides, and any other preparatory-type instruments or guidance-type instruments necessary to effectuate implantation. In an exemplary embodiment, the instruments 220 are custom-made for the particular patient based on the previously-collected anatomical data and previously-completed data comparison. The instruments 220 and implant 210 may be configured for a particular surgical application, such as a total knee application including femoral component 230, tibial baseplate 240 and tibial bearing component 250, together with drill guides and/or cut guides 260, 270, 280, 282. Other tools including moving parts, such as pin handling tool 284, may be included in the surgical kit, in either disposable/recyclable form or reusable/sterilizable form. Moreover, it is contemplated that any other application may be made into a kit in accordance with the present disclosure, including at least one of a unicompartmental knee application, a hip application, an extremity application such as an elbow, shoulder, or ankle, a spine application, a dental application, a sports medicine application, or any other surgical application required.

Exemplary methods and apparatuses for packaging medical instruments are disclosed in U.S. Pat. No. 7,320,404, filed Aug. 10, 2005 and entitled MEDICAL PACKAGING and U.S. patent application Ser. No. 12/331,016, filed Dec. 9, 2008 and entitled METHOD AND APPARATUS FOR PACKAGING MEDICAL DEVICES, both of which are commonly assigned with the present application, the entire disclosures of which are hereby expressly incorporated by reference herein.

The container may then be sealed and sterilized at Step 80. The container and its contents may be sterilized at the manufacturer or at the end user location, such as a hospital or clinic. Alternatively, the case may be sterilized at an intermediate location. In the illustrative embodiment of FIG. 2, seal 290 may be applied to the upper open rim 300 of container 200 in an airtight fashion, thereby hermetically sealing implant 210 and instruments 220 within container 200. Seal 290 may be made of a foil or plastic material, for example, and may be adhesively attached to rim 300. Lid 310 may then be connected to container 200 for later resealing of used contents, as described in greater detail below.

The implant kit is shipped directly to the customer at Step 90. As described above, the customer may be an individual surgeon. However, in other exemplary embodiments, the customer may be a hospital or other healthcare provider. Once the kit is received by the customer, the kit may be brought into an operating room where the patient has been prepped and the joint opened per standard procedures. As indicated above and illustrated in FIG. 2, contained within the individual kit are all of the instruments 220 necessary for implantation of the desired implant 210. The contents of the kit are accessed by removal of lid 310, and peeling away of seal 290.

Figure 2:
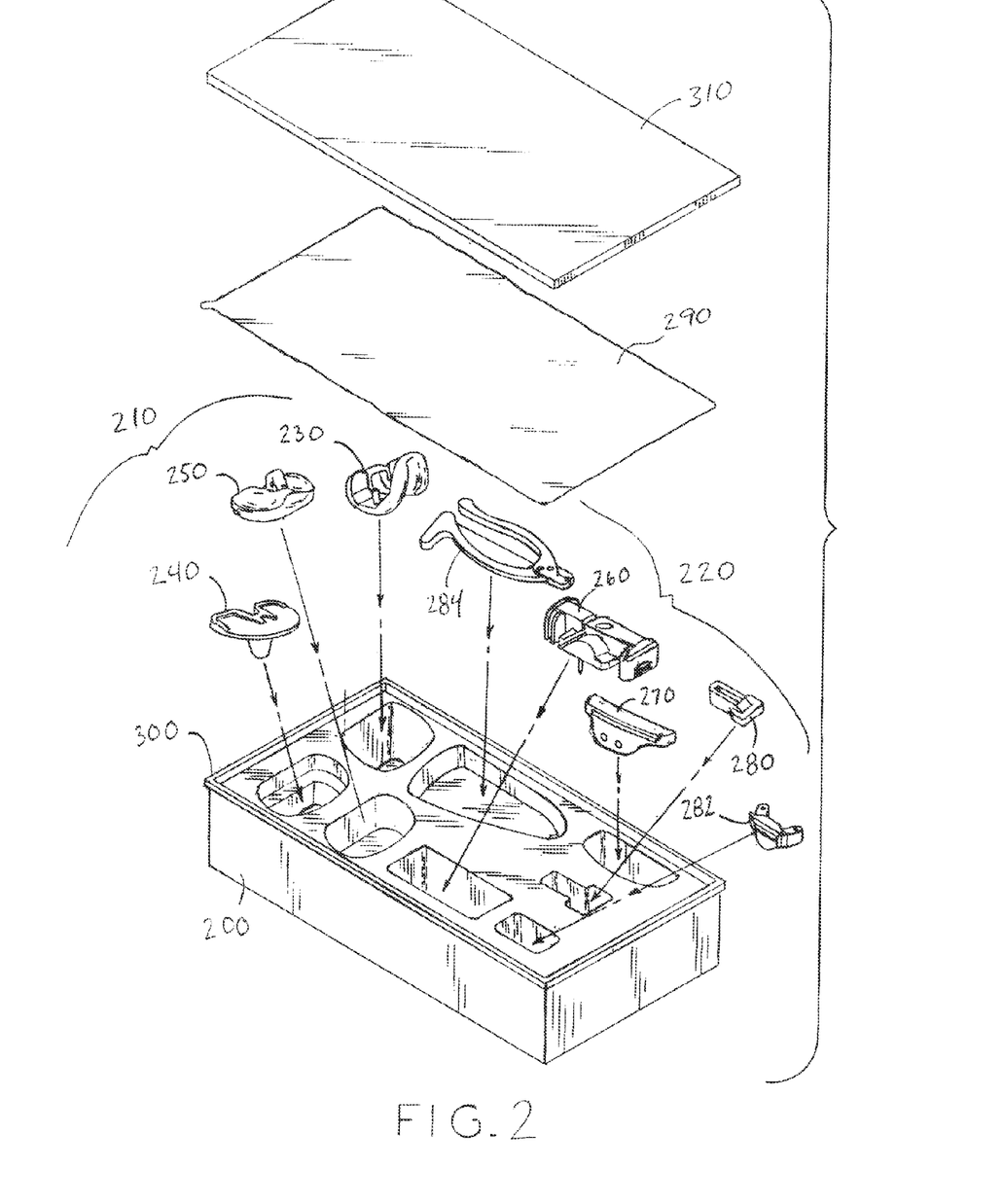
FIG. 2 is a perspective view of a surgical kit made in accordance with the present disclosure.

At Step 100, implant 210 is then implanted. As noted above, the surgeon may specify a preferred surgical technique as part of the data provided to the implant manufacturer. When such information has been provided, the kit may include a customized selection of instruments 220 based upon the surgeon's preselected surgical technique.

After the surgery is completed, an individual within the operating room, such as a scrub nurse, may return the used instruments 220 to the container 200 and replace lid 310 to seal the kit in a closed condition at Step 110. The sealed kit may then be returned to a central receiving location, such as the manufacturer, at Step 120. Once received by the central receiving location, the instruments 220 and container 200 may be processed, such as by recycling the instruments 220 and container 200 so that the entire kit is recycled at Step 130. Alternatively, container 200 and/or one or more of instruments 220 may be sterilized and reused. In an exemplary embodiment, the central receiving location and manufacturing/warehousing location will be the same, such that surgical kits can be prepared, distributed, received and sterilized/disposed of efficiently. For worldwide service, multiple central receiving locations may be provided in certain regions, i.e., the United States, Europe and Asia, in order to reduce logistical constraints and facilitate rapid processing of implant orders and returns.

Advantageously, by utilizing the process of the present disclosure, the kit and instruments used to perform an individual patient's surgery may be disposed of in an environmentally friendly manner. Additionally, the need for a hospital to inventory and track the individual instruments is eliminated. Providing a single kit containing all of the instruments and implant also streamlines surgical preparation procedures, as it eliminates the need for a surgeon or other operating room personnel to identify and collect all of the individual instruments from various locations throughout a facility.

Utilizing a system and/or method in accordance with the present disclosure, an individual patient is provided with an implant that best matches the patient's individual anatomy and accommodates the preferred surgical techniques of the surgeon.

Additionally, the manufacturer and distributors are no longer required to stock a significant amount of inventory, such as a plurality of individual sizes of each individual implant design and/or component, which reduces the need for ample storage space and decreases overall inventory costs.

Further, implant upgrades or design innovations may be inexpensively, quickly and easily incorporated into the instruments and/or implants, as the implants need not be stockpiled in significant quantities and instrument sets are not reused. Thus, each individual surgery is provided with the most up-to-date instruments currently available.

By allowing the instruments to return to a central receiving location, the need to sterilize or otherwise clean the instruments at the location of use is eliminated.

The systems described herein may utilize an online or network-based management system to track, communicate, and otherwise manage the entire process from image acquisition to instrument return. The online management system 400 may utilize mobile devices, such as an iPhone or iPad device, to interface with the system, thereby providing an easy-to-use interface for the surgeon.

Figure 3:
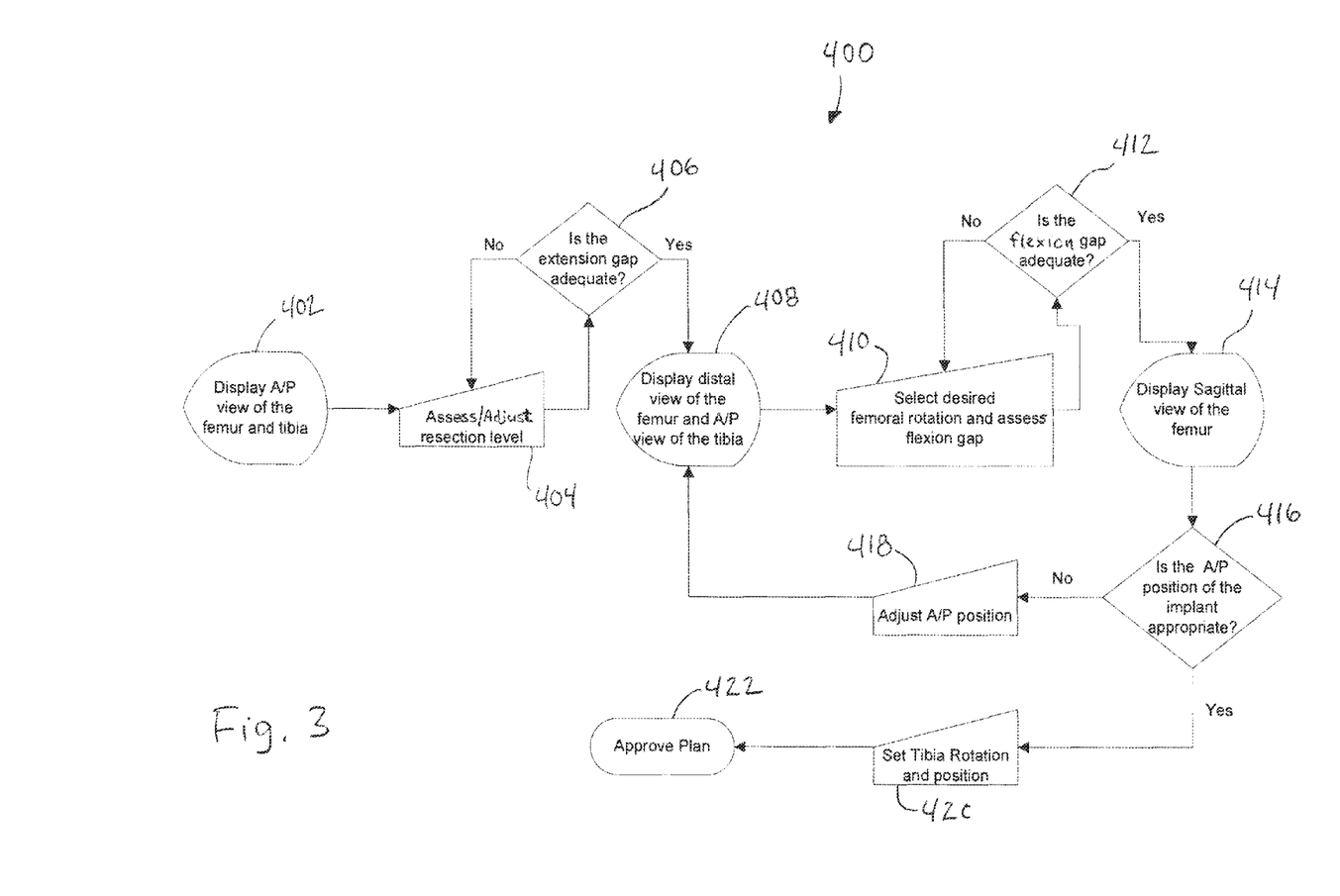
FIG. 3 is a flow chart illustrating an implant planning tool in accordance with the present disclosure.

Turning to FIG. 3, for example, online management system (OMS) 400 may use a joint reconstruction planning wizard which guides a surgeon through a step-by-step approach from acquiring the image, to planning the surgery, to a virtual implantation, to final ordering and return of the components used for the surgery. OMS 400 begins by displaying an anterior and/or posterior view of the femur and tibia of the patient at step 402. The display may be created from pre-operative imaging, as discussed above, and may initially display the femur and tibia in a fully extended orientation.

Presented with this display, the surgeon then assesses and virtually adjusts proposed resections of the femur and tibia at step 404, in accordance with the surgeon's preference. Based on these resections, the OMS 400 selects one or more proposed implants, and these selected implants are superimposed on the virtually resected femur and tibia. The surgeon may then assess, at step 406, whether the extension gap—i.e., the space between the femoral and tibial implant components in full extension—is satisfactory. If the extension gap is too large or too small, OMS 400 reverts to step 404 and a different resection profile and/or implant may be selected iteratively until the extension gap is satisfactory. Once the extension gap is satisfactory, OMS 400 advances to flexion gap assessment as described below.

At step 408, the femur and tibia are again displayed to the surgeon, this time showing the anterior and/or posterior view of the tibia and the distal view of the femur in flexion. The surgeon then selects one or more desired rotational orientations of the femur at step 410, i.e., various rotational orientations associated with flexion of the knee. At step 412, with the virtual knee "flexed," the flexion gap—i.e., the space between the femoral and tibial implant components in a state of flexion—is assessed. If the flexion gap is too large or too small, OMS 400 reverts to step 410 and a different flexion level and/or implant may be selected iteratively until the flexion gap is satisfactory. The profile of one or more of the femur resections may also be iteratively adjusted, such as the cuts on the posterior portion of the femoral condyles. Once the flexion gap is satisfactory, OMS 400 advances to implant antero-posterior position assessment as described below.

At step 414, the femur and tibia are again displayed to the surgeon, this time showing a sagittal view of the tibia and femur. The surgeon then assesses, at step 416, the antero-posterior position of the previously-chosen implant components. If the antero-posterior positions of the components relative to one another and to their respective bones are not satisfactory, the surgeon adjusts such positioning at step 418 and OMS 400 reverts back to step 408 to begin reassessment of the flexion gap as described above. This process is iteratively repeated until the flexion gap and antero-posterior position of the implants are both satisfactory.

OMS 400 then advances to step 420, where tibial rotation and position are set by the surgeon according to his or her preference. With all parameters needed for the manufacture of implant 210 as discussed above, the surgical plan and implants are approved at step 422 and a surgical kit in accordance with the present disclosure may be ordered.

Online management system 400 simplifies processes, advantageously employs current technology, reduces surgeon input time, manages inventory, reduces costs for the manufacturer, and provides the patient with a quicker and more efficient process for their surgery.

While this disclosure has been described as having an exemplary design, the present invention can be further modified within the spirit and scope of this disclosure. This application is therefore intended to cover any variations, uses, or adaptations of the disclosure using its general principles. Further, this application is intended to cover such departures from the present disclosure as come within known or customary practice in the art to which this disclosure pertains and which fall within the limits of the appended claims.

What is claimed is:

1. A method of ordering and manufacturing an implant and related instruments for a specific patient, comprising the steps of:
   receiving anatomical data collected from the specific patient;
   comparing the anatomical data to a database including a plurality of implant designs;
   identifying an implant design from the plurality of implant designs based on a result of said step of comparing the anatomical data to the database;
   manufacturing an implant based on the identified implant design;
   manufacturing an instrument for use in implanting the implant;
   sealing the implant and the instrument in at least one container, the at least one container comprising a recyclable material, including using a separable, resealable lid to cover the at least one container;
   contemporaneously shipping the implant and the instrument in the at least one container;
   receiving, at the manufacturer's receiving location, the at least one container having the resealable lid resealed thereon and the instrument enclosed therein, after the instrument has been used; and
   recycling the recyclable material of the at least one container so that the at least one container is not reusable.

2. The method of claim 1, wherein the instrument involved in said steps of sealing and contemporaneously shipping is an unused instrument.

3. The method of claim 1, wherein the at least one container comprises a single container and said step of sealing comprises sealing the implant and the instrument in the single container.

4. The method of claim 1, wherein the instrument comprises a recyclable material, the method further comprising, after said step of receiving, the additional step of:
   recycling the recyclable material of the instrument.

5. The method of claim 4, wherein said step of recycling the recyclable material of the at least one container immediately follows said step of receiving the at least one container.

6. The method of claim 1, further comprising the step of sterilizing the at least one container before, after, or both before and after said step of shipping.

7. The method of claim 1, wherein sealing the implant and the instrument in the at least one container further includes applying a hermetic seal to the at least one container.

8. The method of claim 1, further comprising the step of disposing of at least a disposable part of the at least one container and a disposable part of the instrument.

9. The method of claim 1, wherein said step of manufacturing an implant follows said step of receiving anatomical data.

10. The method of claim 1, wherein said step of manufacturing an implant comprises manufacturing a custom implant for the specific patient based on the received anatomical data.

11. The method of claim 1, wherein said step of manufacturing an implant comprises:
    selecting an implant from a stock of implants, the selected implant having a material thickness greater than an implant based on the identified implant design;
    receiving the identified implant design; and
    removing material from the selected implant to provide a custom implant for the specific patient corresponding to the identified implant design.

12. The method of claim 1, wherein the plurality of implant designs comprise a plurality of validated implant designs, said step of manufacturing an implant comprising the step of manufacturing an implant based on one of the plurality of validated implant designs.

13. The method of claim 1, wherein the step of identifying an implant design comprises the step of templating.

14. A method of ordering and manufacturing an implant and related instruments for a specific patient, comprising the steps of:
    receiving anatomical data collected from the specific patient;
    comparing the anatomical data to a plurality of implant designs, including identifying a best-fit implant design from the plurality of implant designs, based on the anatomical data;
    selecting the best-fit implant design based on a result of the step of comparing;
    manufacturing an implant for the specific patient after the step of selecting, the implant corresponding to the best-fit implant design;
    manufacturing an instrument for use in implanting the implant;
    enclosing the implant and the instrument in at least one container, the at least one container comprising a recyclable material, wherein enclosing includes covering the container with a hermetic seal and a resealable lid;
    contemporaneously shipping the implant and the at least one instrument in the at least one container;
    receiving, at the manufacturer's receiving location, the at least one container having the resealable lid resealed thereon and the instrument enclosed therein after the instrument has been used; and
    recycling the recyclable material of the at least one container, after the step of receiving, so that the at least one container is not reusable.

15. The method of claim 14, wherein the plurality of implant designs comprises a plurality of virtual models of predesigned, tested and validated implant designs.

16. The method of claim 14, wherein the step of manufacturing an implant for the specific patient comprises:
    providing a previously manufactured implant having a material thickness;
    receiving the best-fit implant design; and
    removing material from the previously manufactured implant so that the previously manufactured implant conforms to the best fit implant design.

17. The method of claim 14, wherein the step of comparing includes keying a virtual model of an implant design to a data record for a best-fit implant design.

18. The method of claim 14, wherein the anatomical data comprises a motion of an articular surface of a joint as the joint is articulated through a range of motion.

19. The method of claim 14, wherein the instrument comprises at least one recyclable part including a recyclable material, the method further comprising, after the step of receiving, recycling the recyclable material of the at least one recyclable part so that the at least one recyclable part is not reusable.

* * * * *